DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED JULY 1, 1975

936 O.G. 7

T936,003

STABILIZATION OF α,α-DISUBSTITUTED-β-PROPIOLACTONES

Windell C. Watkins, 1605 Auburn Drive, Longview, Tex. 75601, and James J. Ward, Rte. 1, Box 108B, Henderson, Tex. 75652

Continuation of abandoned application Ser. No. 205,763, Dec. 7, 1971. This application May 2, 1974, Ser. No. 466,363

Int. Cl. C07d *3/00*

U.S. Cl. 260—343.9

No Drawing. 10 Pages Specification

α,α-Disubstituted-β-propiolactone having the general formula

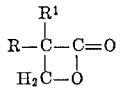

wherein R and $R^1$ are selected from the group consisting of hydrogen, straight- or branched-chain alkyl groups of from 1 to 10 carbon atoms, substituted or unsubstituted cyclic hydrocarbon groups of from 6 to 10 carbon atoms, or wherein R and $R^1$ join to form a ring of from 6 to 10 carbon atoms, are effectively stabilized against premature polymerization during storage by including in admixture therewith a stabilizing amount of a hydroquinone monoalkyl ether having the general formula

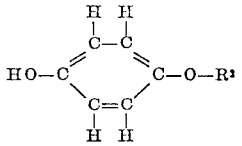

wherein $R^2$ is a straight-, branched-chain, or cyclic alkyl group of from 1 to 10 carbon atoms.